(12) United States Patent
Sherrill et al.

(10) Patent No.: US 9,695,177 B2
(45) Date of Patent: Jul. 4, 2017

(54) PREPARATION OF TETRANITROGLYCOLURIL

(71) Applicant: U.S. Army Research Laboratory ATTN: RDRL-LOC-I, Washington, DC (US)

(72) Inventors: William Matthew Sherrill, Aberdeen, MD (US); Eric Christopher Johnson, Millington, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 85 days.

(21) Appl. No.: 14/499,278

(22) Filed: Sep. 29, 2014

(65) Prior Publication Data

US 2016/0176878 A1    Jun. 23, 2016

(51) Int. Cl.
*C06B 25/34*  (2006.01)
*C06B 45/00*  (2006.01)
*C07D 487/04* (2006.01)

(52) U.S. Cl.
CPC .......... *C07D 487/04* (2013.01); *C06B 25/34* (2013.01); *C06B 45/00* (2013.01)

(58) Field of Classification Search
CPC ........ C07D 487/04; C06B 45/00; C06B 25/34
See application file for complete search history.

(56) References Cited

U.S. PATENT DOCUMENTS 4,487,938 A     12/1984  Boileau
9,512,127 B2 *  12/2016  Sherrill ................ C07D 487/04

* cited by examiner

*Primary Examiner* — Aileen B Felton
(74) *Attorney, Agent, or Firm* — Robert Thompson

(57) ABSTRACT

An improved method of preparing tetranitroglycoluril (TNGU) via the in situ decomposition of a nitrimino group with elimination of nitrogen without the use of dinitrogen pentoxide. The compound is useful as a high energy, high density explosive or propellant oxidizer.

14 Claims, 3 Drawing Sheets

1

$C_4H_2N_8O_{10}$
MW: 322.1063

1

C₄H₂N₈O₁₀
MW: 322.1063

Reaction Pathway for the Production of structure 1 above

Proposed Structure of Intermediate 5 Formed in *situ* under the Nitration Conditions Proposed Intramolecular Degradation Pathway with Elimination of $N_2O$ (g)

Proposed Intermolecular degradation Pathway with Elimination of 2 $N_2O_{(g)}$

PREPARATION OF TETRANITROGLYCOLURIL

GOVERNMENT INTEREST

The embodiments described herein may be manufactured, used, and/or licensed by or for the United States Government without the payment of royalties thereon.

BACKGROUND

Field of Use

The embodiments described herein generally relate to the chemistry of high energy materials and process methods thereof. Embodiments are also of use in applications requiring a high performing military grade explosive. Tetranitroglycoluril (TNGU) has a detonation performance exceeding Octahydro-1,3,5,7-tetranitro-1,3,5,7-tetrazocine (HMX) and could potentially be used in many of the same types of high energy applications.

Known polynitramines such as 1,3,5-trinitro-1,3,5-hexahydrotriazine (RDX) and 1,3,5,7-tetranitro-1,3,5,7-tetraazacyclooctane (HMX) are high-energy, high-density explosive compounds (R. Meyer, "Explosives," Third edition, VCH Publishers, Weinheim, Germany, 1987). They can be prepared nitrolysis of hexamine with acid and other similar procedures. RDX was first synthesized in 1906 by Brunswig (German Patent No. 299,028). RDX came into significant use during World II. RDX has a very good thermal stability. It under goes no decomposition below 100° C. It begins to decompose only at a temperature above about 160 to about s170° C. Under vacuum and after 40 hours, only 0.2 and 0.8 $cm^3$ of gases evolve from a one gram sample of RDX at respectively 102° C. and 150° C. It melts with decomposition at 204° C., but its explosion temperature measured by heating at the rate of 5° C. per minute is 260° C. The density of hexogen (RDX) is very high. The crystal density (theoretical density) is 1.82 $g/cm^3$ at 20° C. but its highest practical density is only 1.72 $g/cm^3$. Its rate of detonation is 8,800 m/s at the theoretical density and 8,520 m/s at the highest practical density.

HMX was only discovered and recognized as a valuable explosive during World War II. Octogen (HMX) has a very good thermal stability. It undergoes no decomposition below 100° C. It begins to decompose at a temperature higher than that of Hexogen (RDX). Under vacuum and after 40 hours only 0.08, 0.09, and 0.12 $cm^3$ of gases evolve from a one gram sample at respectively 100, 120, and 150° C. Octogen (HMX) melts with decomposition at 280° C. but its explosion temperature measured by heating at the rate of 5° C. per minute is 330° C.

The density of octogen is one of the highest reported for a crystalline high explosive. The crystal density is 1.91 $g/cm^3$ at 20° C. for the β-stable crystalline form but the highest practical density obtained by compression of powdered octogen is 1.84 $g/cm^3$. At this density, its rate of detonation is 8,850 m/s.

In embodiments one object of the present invention is to provide Tetranitroglycoluril from Imidazo-[4,5-d-imidazoles with the loss of dinitrogen oxide.

Research in the field of higher performing explosives for military use commenced with WWI and by the 2nd World War both pentaerythritol tetranitrate (PETN) and cyclotrimethylenetrinitramine (RDX) were investigated. RDX found greater use because it is less sensitive and more powerful than PETN.

The entirety of energetic materials is defined by the American Society for Testing and Material (ASTM) as " . . . a compound or mixture of substances which contains both the fuel and the oxidizer and reacts readily with the release of energy and gas . . . ".[3] Energetic materials themselves are then divided into three unique classes: explosives, propellants and pyrotechnics. The class of explosives can be divided further into primary and secondary explosives.

Primary explosives are very sensitive explosives, which can be easily initiated by friction, impact, spark or heat. The initiation of primary explosives leads to a fast deflagration to detonation process with a shock wave formed, which is able to set off the less sensitive charge (main charge, secondary explosive) of an explosive device. They undergo a very fast deflagration to detonation transition (DDT) and are therefore used in initiating devices. Common primary explosives are lead(II) azide, lead(II) styphnate and mercury fulminate. The obvious disadvantage of these compounds is the toxicity of the heavy metal cations. Therefore, new less toxic primary explosives based on organic, metal free compounds were investigated and developed. Besides the development of metal free organic primaries, the replacement of the toxic cations with less toxic metals like silver, iron or copper is another topic of current interest.

Secondary explosives are not only much more stable in terms of friction, impact and electrostatic discharge, but also kinetically stable (metastable) compounds. Hence, they have to be ignited by much larger stimuli, mostly generated by a primary charge. After initiation by the detonation shockwave of primary explosives, the secondary explosive generates a shockwave which promotes the reaction front through the unreacted material. Although they need a much higher impetus to be detonated, secondary explosives exhibit much higher performances than primary explosives. Common secondary explosives are TNT, RDX, HMX, TATB and NQ.

SUMMARY

In embodiments, this disclosure provides new methods for the synthesis of tetranitroglycoluril (TNGU) via the rearrangement of the nitrimines with the release of dinitrogen oxide. TNGU having the structure 1 is produced

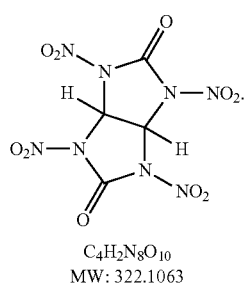

1

$C_4H_2N_8O_{10}$
MW: 322.1063

In embodiments, the instant application discloses a novel method for the synthesis of tetranitroglycoluril (TNGU) which produces TNGU having a much improved sensitivity profile compared to material produced according to the prior art.

It would be advantageous to provide an alternative method for preparing tetranitroglycoluril (TNGU) with improved chemical and physical properties.

This new methodology makes use of in situ degradation of nitrimino moieties found in three different starting materials: N,N'-dinitrotetrahydroimidazo[4,5-d]imidazole-2,5(1H,3H)diimine, N-nitrotetrahydroimidazo[4,5-d]imidazole-2,5(1H,3H)diimine hydrochloride, and N-nitrotetrahydroimidazo[4,5-d]imidazole-2,5(1H,3H)diimine nitrate with the subsequent release of dinitrogen oxide gas from a nitration mixture composed of trifluoroacetic anhydride and nitric acid. The impact sensitivity of the material produced via the new method was measured to be 11.07 inches using the Langlie one shot $H_{50}$ method, friction was measured at 70 N using a BAM friction apparatus, and electrostatic discharge was measured at 3.25 J. This is compared to 4.10 inches for dropweight, 54 N for friction and 3.25 J obtained from batches of TNGU produced according to prior art procedures.

The process for the production of TNGU from the rearrangement of the nitrimines with the release of dinitrogen oxide has not been previously documented. This coupled with the improvement in the sensitivity profile of the material produced from the new process make it a formidable compound for military purposes.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description.

The embodiments of the present invention provide for a method for synthesizing tetranitroglycoluril (TNGU). More specifically this new methodology makes use of in situ degradation of nitrimino moieties found in three different starting materials: N,N'-dinitrotetrahydroimidazo[4,5-d]imidazole-2,5(1H,3H)diimine, N-nitrotetrahydroimidazo[4,5-d]imidazole-2,5(1H,3H)diimine hydrochloride, and N-nitrotetrahydroimidazo[4,5-d]imidazole-2,5(1H,3H)diimine nitrate with the subsequent release of dinitrogen oxide gas from a nitration mixture composed of trifluoroacetic anhydride and nitric acid. The impact sensitivity of the material produced via the new method was measured to be 11.07 inches using the Langlie one shot $H_{50}$ method, friction was measured at 70 N using a BAM friction apparatus, and electrostatic discharge was measured at 3.25 J. This is compared to 4.10 inches for dropweight, 54 N for friction and 3.25 J obtained from batches of TNGU produced according to literature procedures.

TNGU produced by the disclosed method is greater than twice as stable to external insult than TNGU synthesized according to the prior art. This difference in sensitivity profile makes the material isolated from the new process inherently more stable to handle and process than material isolated from the prior art methods.

This material is envisioned to be of use in applications requiring a high performing military grade explosive. TNGU has detonation performance exceeding HMX and as such could potentially be used in many of the same types of applications.

Figure 1:
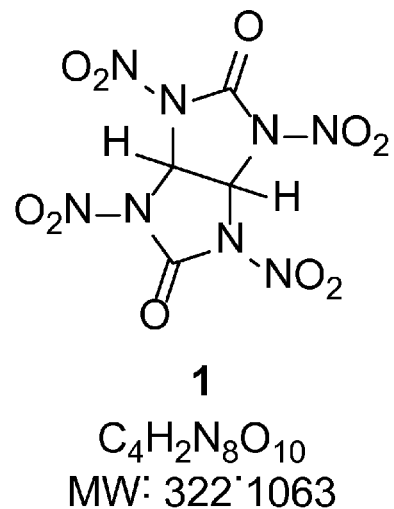
FIG. 1 illustrates a chemical structure for tetranitroglycoluril (TNGU or Sorguly,1)
Figure 2:
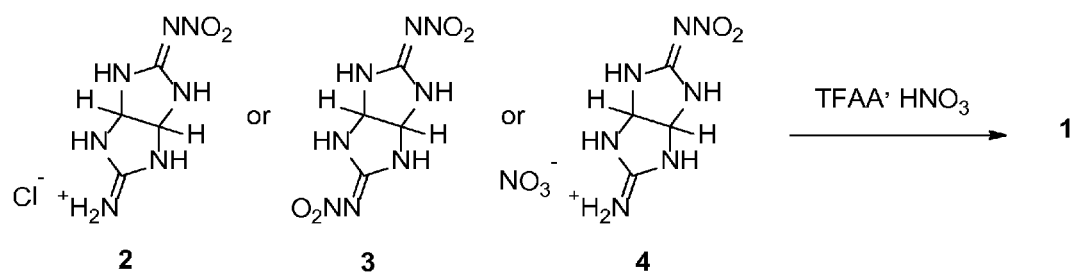
FIG. 2 illustrates the production pathway for producing TNGU.
Figure 3:
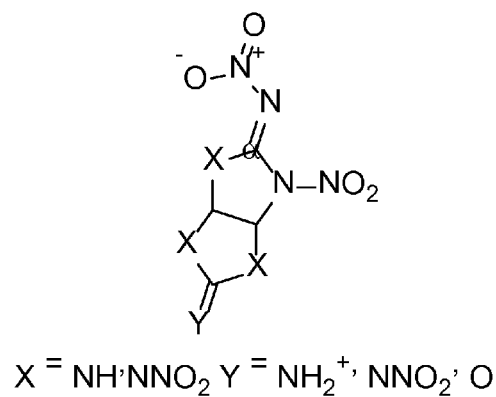
FIG. 3 illustrates a proposed structure of the intermediate 5 formed in situ under nitration conditions.

According to embodiments of the process, TNGU (FIG. 1) is produced from the nitration of N-nitrotetrahydroimidazo[4,5-d]imidazole-2,5(1H,3H)diimine hydrochloride, as shown in structure 2 in FIG. 2. TNGU may also be produced according to embodiments of the present disclosure from the nitration of N,N'-dinitrotetrahydroimidazo[4,5-d]imidazole-2,5(1H,3H)diimine, structure 3 in FIG. 2 or from the nitration of N-nitrotetrahydroimidazo[4,5-d]imidazole-2,5(1H,3H)diimine nitrate structure 4 in FIG. 2 in a mixture of trifluoroacetic anhydride and a greater than 99.5% $HNO_3$ in yields typically from about 45 to about 65 percent.

TABLE 1

Performance Predictions from Cheetah 6.0 Thermochemical Computer Code

| Substance | Density | $\Delta H_f$ (kJ/mol) | $P_{cj}$ (GPa) | $D_v$ (km/s) | $\Delta H_d$ (kJ/mL) | OB (%) |
|---|---|---|---|---|---|---|
| Structure 1 | 2.01 | 50.0 | 41.98 | 9.557 | 11.78 | +4.97 |
| RDX | 1.816 | 70.01 | 33.42 | 8.858 | 10.41 | −21.61 |
| HMX | 1.90 | 75.02 | 37.159 | 9.243 | 11.01 | −21.61 |

Figure 4:
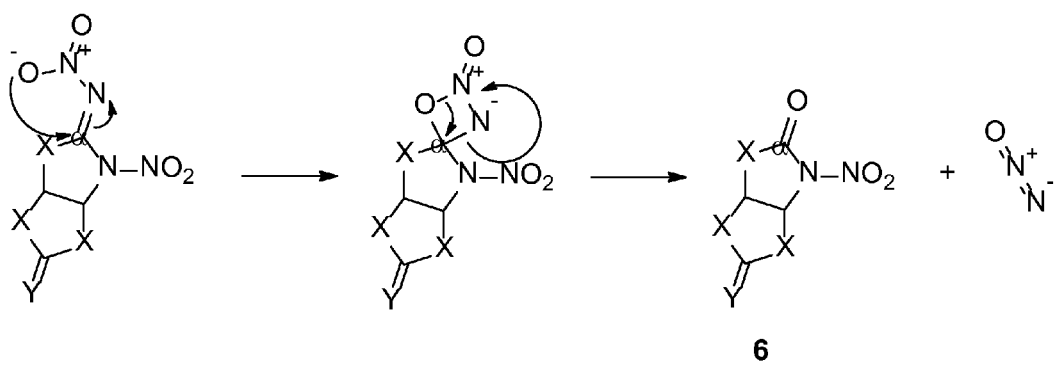
FIG. 4 illustrates a proposed intramolecular degradation pathway showing the elimination of $N_2O$.
Figure 5:
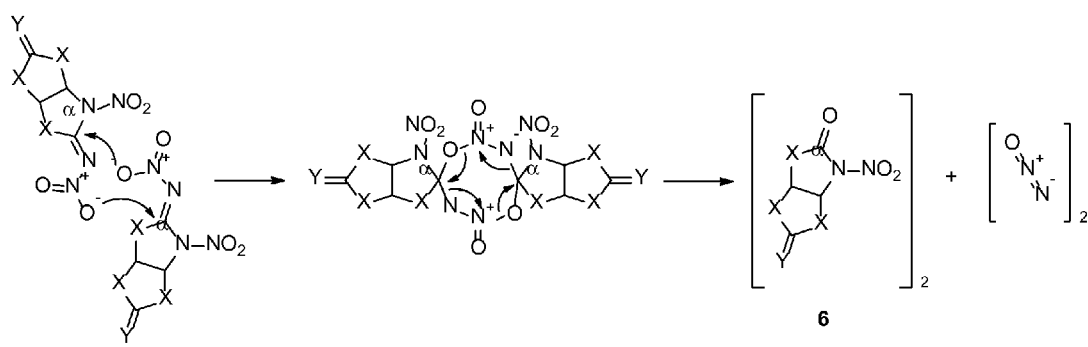
FIG. 5 illustrates an additional proposed intermolecular degradation pathway with elimination of 2 $N_2O_{(g)}$.

The slow addition of TFAA to a solution of structures 2, 3, or 4 in greater than or equal to 98% $HNO_3$, is believed to generate a species similar to structure 5 from all three starting materials. Due to the electron withdrawing natures of both the nitrimine and the nitramine of structure 5, the carbon center is highly susceptible to nucleophilic attack either intra- or intermolecularly by a nucleophile like the oxygen of the nitrimine. Both of the proposed intra- and intermolecular degradation pathways are illustrated in FIG. 4 and FIG. 5. This intra- or intermolecular attack is envisioned to result in the formation of structure 6 and the liberation of $N_2O$ gas which can be observed in the headspace of the reaction mixture through FTIR analysis. Once this decomposition has occurred on one of the imidazolimine rings to generate imidazolidinone of structure 6, the process is repeated on the other ultimately resulting in the formation of structure 1. $N_2O$ gas is not observed at a concentration higher than normal background for the nitration mixture in the headspace of reactions to produce structure 1 employing literature methods using glycoluril as a feedstock. This decomposition of the nitrimine with liberation of $N_2O$ gas is the feature of this process which makes it unique from other methods using glycoluril as a feedstock.

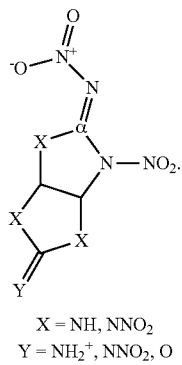

X = NH, NNO$_2$
Y = NH$_2^+$, NNO$_2$, O

The impact sensitivity of the material produced via the new method was measured to be 11.07 inches using the Langlie one shot H$_{50}$ method, friction was measured at 70 N using a BAM friction apparatus, and electrostatic discharge was measured at 3.25 J. This is compared to 4.10 inches for dropweight, 54 N for friction and 3.25 J obtained from batches of TNGU produced according to literature procedures.

TABLE 1

Sensitivity Data

| Substance | Impact (in.)[a] | Friction (N)[b] | ESD (J)[c] |
|---|---|---|---|
| Novel Process 1 | 11.07 | 70 | 3.25 |
| Literature Process 1 | 4.10 | 54 | 3.25 |
| RDX | 9.08 | 120 | 0.625 |
| HMX | 9.08 | 120 | 0.025 |

EXAMPLES

Precursors, shown as structures 2 through 4 in FIG. 2 were prepared according to the process described in the prior art literature, for example: Kony, M.; Dagley, I. J. Heterocycles 1994, 38, 595-600.

NMR spectra were recorded on a Brüker 600 MHz NMR with acetone-d6 as the solvent. All NMR chemical shifts are reported in ppm relative to TMS-Cl. FTIR spectra were recorded using a Brüker Alpha-T fitted with a diamond ATR (DATR) cell. Headspace FTIR was recorded using a Brüker Alpha-T fitted with a transmission cell module equipped with an IR gas flow cell (5 cm path length) equipped with ZnSe windows using N$_2$ as the carrier gas at a flow rate of 12 mL/min. Samples (6 mL) of the headspace from the nitration mixture were injected into the N$_2$ and analyzed for the N$_2$O doublet at approximately 2230 cm$^{-1}$. Density was measured using gas pycnometry on a Micromeritics Accu-Pyc 1330 using helium as the analysis gas. Differential scanning calorimetry (DSC) was performed on a Tainstruments (TA) model Q10 or Q20 calorimeter calibrated to the melting point of indium. H$_{50}$ values for drop weight testing were determined using the Langlie one-shot method on a tester dropping a 5 pound weight from a maximum height of 60 inches. Friction sensitivity measurements were determined on a BAM friction tester and ESD was determined using an ABL ESD apparatus. All deuterated solvents were obtained from Cambridge Isotope Laboratories, Andover, Mass., USA.

Example 1

A typical procedure for the production of 1 at the 1 g scale from structure 2:
To a clean, oven dried 100 mL flask equipped with a nitrogen line, magnetic stirring bar, 50 mL dropping funnel, and a drying tube charged with CaCl$_2$, is added 1.0995 g (4.96 mmol) of structure 2. To this is added 20 mL of trifluoroacetic anhydride. 20 mL of greater than or equal to 99.5% HNO$_3$ is added to the addition funnel and the system is then purged with nitrogen and cooled to 0° C. by means of an ice bath. The nitric acid is added slowly; drop wise in 4 equally spaced increments with each increment lasting 15 minutes each and added over the course of two hours. Cooling and stirring is maintained throughout the entire addition. At this point, all of the solids have dissolved, and the solution is yellow and homogenous. The flask is removed from the ice bath and allowed to warm to room temperature or about 25° C., with stirring for an additional 2 hours. During this time, N$_2$O gas evolution can be observed with subsequent precipitation of structure 1 from the reaction mixture. Once the two hour period at room temperature has elapsed, the stirring is stopped and the material is allowed to settle to the bottom of the flask. The nitration mixture is then decanted from the product. The material is washed with dry dichloromethane (DCM) from about six (6) to about ten (10) times by suspending the solid in from about 20 to about 30 mL of DCM, allowing the solid to settle out, and decanting the supernatant. The solid is then evaporated to dryness by passing dry, inert gas (N$_2$) over the material until the residual DCM has evaporated followed by vacuum drying (10 torr) for 1 hr at ambient temperature. The yield on this process is 1.128 g (2.75 mmol, 55%) of a snow white powder with decomposition and spectral analysis matching what has been previously published in literature.
1H NMR (600.18 MHz, Acetone-D6) 7.76 (s, 2H); 13C NMR (150.91 MHz, Acetone-D6) 142.61, 66.14; FTIR (DATR),n=2997, 1798, 1652, 1617, 1594, 1369, 1255, 1144, 1090, 808, 754, 730, 398.

Example 2

A typical procedure for the production of structure 1 at the 1 g scale from structure 3: Same as above procedure, 1.0765 g (4.67 mmol) of structure 3. The yield obtained from structure 3 was 0.7852 g (2.43 mmol, 52%). The appearance and spectral analysis of the material recovered matched that from the typical procedure above.

Example 3

A typical procedure for the production of structure 1 at the 1 g scale from 4: Same as above procedure, 0.9986 g (4.02 mmol) of 4. The yield of 1 obtained from 4 was 0.7523 g (2.33 mmol, 57%). The appearance and spectral analysis of the material recovered matched that from the typical procedure above.
Properties of structure 1 obtained via our method:
Density=2.04 g/mL measure by He gas pycnometry
DSC decomposition: 210-220° C. at 10° C./min
Impact sensitivity: 11.07"
BAM Friction sensitivity: 63 N
Electrostatic discharge (ESD): 3.25 J
Oxygen balance: +4.97%
The original patent for structure 1 was granted in 1984 to J. Boileau. His synthetic methodology for successfully achieving structure 1 was the direct nitration of glycoluril using a mixture of $N_2O_5$ and 100% $HNO_3$. The yields on his process are claimed to be greater than 85%. It has since been discovered it is possible to successfully synthesize structure 1 using a mixture of acetic anhydride and 100% $HNO_3$ in similar yields without necessitating the making of $N_2O_5$ directly. Both methods yield structure 1 that is highly sensitive to impact and friction (approximately twice more sensitive on both accounts than standard military explosives RDX and HMX) making handling of the material from these processes inherently more dangerous.

Using the new method, structure 1 is readily accessible in three steps from commercially available materials via an alternative route than what is currently known in the art. In addition, the material isolated from this new method, has a 11.07" $H_{50}$ impact value relative to the material isolated from the current literature method having a 4.10" impact value when both are measured using our impact testing device. This coupled with the fact that each step is done near ambient conditions further increases the attractiveness of this procedure.

Example 4

Procedure From N-nitrotetrahydroimidazo[4,5-d]imidazole-2,5(1H,3H)diimine Hydrochloride:

100 mg (0.45 mmol) of the chloride salt was dissolved in 2 mL of 100% $HNO_3$ at 0° C. under an inert $N_2$ atmosphere. To this solution was added 2 mL of TFAA drop wise at such a rate as to keep the temperature of the solution below 10° C. After the addition was completed, the reaction was allowed to warm to room temperature or about 25° C. and stirred for 2 hours at which point stirring was stopped and the precipitant was allowed to settle. The mother liquor was decanted, and the residual solid was washed with about five (5) milliliters of anhydrous DCM from about five (5) to about seven (7) times. The solid TNGU was then dried under vacuum (10 torr) at ambient temperature for 2 hours. The total amount of TNGU recovered from this process was 70.1 mg (0.22 mmol, 49%) Peak decomposition was observed to be 217-220° C. in the DSC. $^1$H NMR (600.182 MHz, Acetone-$D_6$) 7.78 (s, 2H); $^{13}$C NMR (150.046 MHz, Acetone-$D_6$) 141.8, 65.3; FTIR (DATR),ñ=2997, 2894, 1798, 1652, 1617, 1594, 1255, 1144, 1090, 768, 730, 698; $C_4H_2N_4O_{10}$: calcd C, 14.92; H, 0.63; N, 34.79%. found: C, 14.89; H, 0.63; N, 34.72%.

Example 5

Procedure From N-nitrotetrahydroimidazo[4,5-d]imidazole-2,5(1H,3H)diimine Nitrate:

100 mg (0.40 mmol) of nitrate salt was dissolved in 2 mL of 100% $HNO_3$ at 0° C. under an inert $N_2$ atmosphere. To this solution was added 2 mL of TFAA drop wise at such a rate as to keep the temperature of the solution below 10° C. After the addition was completed, the reaction was allowed to warm to room temperature and stirred for 2 hours at which point stirring was stopped and the precipitant was allowed to settle. The mother liquor was decanted, and the residual solid was washed with about five (5) milliliters of anhydrous DCM from about five (5) to about seven (7) times anhydrous DCM. The solid TNGU was then dried under vacuum (10 torr) at ambient temperature for 2 hours. The total amount of TNGU recovered was 104 mg (0.32 mmol, 80%).

Example 6

Procedure From N,N'-dinitrotetrahydroimidazo[4,5-d]imidazole-2,5(1H,3H)diimine:

100 mg (0.43 mmol) of the dinitro compound was dissolved in 2 mL of 100% $HNO_3$ at 0° C. under an inert $N_2$ atmosphere. To this solution was added 2 mL of TFAA drop wise at such a rate as to keep the temperature of the solution below 10° C. After the addition was completed, the reaction was allowed to warm to room temperature and stirred for 2 hours at which point stirring was stopped and the precipitant was allowed to settle. The mother liquor was decanted, and the residual solid was washed with about five (5) milliliters of anhydrous DCM from about five (5) to about seven (7) times. The solid TNGU was then dried under vacuum (10 torr) at ambient temperature for 2 hours. The total amount of TNGU recovered 89.2 mg (0.28 mmol, 65%).

Example 7

Scale up to 2 g of TNGU From N-nitrotetrahydroimidazo[4,5-d]imidazole-2,5(1H,3H)diimine nitrate:

2.027 g (8.16 mmol) of nitrate salt was dissolved into 40 mL of 100% $HNO_3$ at 0° C. under an $N_2$ atmosphere. To this solution was added drop wise 40 mL of TFAA at a rate to keep the temperature under 10° C. Upon completion of the addition, the material was allowed to warm to ambient temperature and stirring was continued for about 2 hours. After the time had elapsed, the suspension was cooled to 0° C., stirring was stopped and the suspended solid was allowed to settle. The mother liquor was decanted, and the remaining solid was washed with about five (5) milliliters of anhydrous DCM from about five (5) to about seven (7) times. The material was then vacuum dried (10 torr 20° C.) for 2 hours. The total amount of TNGU recovered from this process was 1.89 g (5.86 mmol, 72%).

The TNGU produced in Examples 1-7 are approximately twice less sensitive to impact events on a dropweight testing apparatus, and approximately one and a half times less sensitive to friction events on friction testing apparatus when compared to prior art methods.

Physcial Properties of structure 1, FIG. 1 obtained via our method:
Density=2.04 g/mL measure by He gas pycnometry
DSC decomposition: 210-220° C. at 10° C./min
Impact sensitivity: 11.07"
BAM Friction sensitivity: 63 N
Electrostatic discharge (ESD): 3.25 J
Oxygen balance: +4.97%

What is claimed is:
1. A process for preparing tetranitroglycoluril (TNGU) via an in situ decomposition of a nitrimino group with elimination of nitrogen without the use of dinitrogen pentoxide comprising:
a nitrimino moiety selected from the group consisting of N,N'-dinitrotetrahydroimidazo[4,5-d]imidazole-2,5 (1H,3H)diimine, N-nitrotetrahydroimidazo[4,5-d]imidazole-2,5(1H,3H)diimine hydrochloride, and N-nitrotetrahydroimidazo[4,5-d]imidazole-2,5(1H,3H) diimine nitrate;
wherein the moiety is dissolved in a from about 1 ml to about 3 ml solution of 100% nitric acid under an inert nitrogen atmosphere and at a temperature of about zero (0) degrees Celsius;

wherein there is added two milliliters of a 100 percent trifluoroacetic anhydride solution drop wise at such a rate as to keep the temperature of the solution below ten (10) degrees Celsius;

further wherein the solution is allowed to warm to from about 20° C. to about 26° C. with stirring for about two (2) hours until the precipitant is settled; and wherein the precipitant is washed with anhydrous dichloromethane, dried under vacuum at 10 torr with a yield of about 70.1 milligrams (0.22 mmol, 49%) of tetranitroglycoluril (TNGU).

2. A process according to claim 1 where the nitrimino moiety comprises N,N'-dinitrotetrahydroimidazo[4,5-d]imidazole-2,5(1H,3H)diimine.

3. A process according to claim 2 wherein the peak decomposition of the TNGU is from about 217 to about 220° C. as measured by a differential scanning calorimeter (DSC).

4. A process according to claim 1 where the nitrimino moiety comprises N-nitrotetrahydroimidazo[4,5-d]imidazole-2,5(1H,3H)diimine hydrochloride.

5. A process according to claim 4 wherein the peak decomposition of the TNGU is from about 217 to about 220° C. as measured by a differential scanning calorimeter (DSC).

6. A process according to claim 1 where the nitrimino moiety comprises and N-nitrotetrahydroimidazo[4,5-d]imidazole-2,5(1H,3H)diimine nitrate.

7. A process according to claim 6 wherein the peak decomposition of the TNGU is from about 217 to about 220° C. as measured by a differential scanning calorimeter (DSC).

8. A process for preparing tetranitroglycoluril (TNGU) via an in situ decomposition of a nitrimino group with elimination of nitrogen without the use of dinitrogen pentoxide comprising:

a nitrimino moiety selected from the group consisting of N,N'-dinitrotetrahydroimidazo[4,5-d]imidazole-2,5(1H,3H)diimine, N-nitrotetrahydroimidazo[4,5-d]imidazole-2,5(1H,3H)diimine hydrochloride, and N-nitrotetrahydroimidazo[4,5-d]imidazole-2,5(1H,3H) diimine nitrate;

wherein the moiety is dissolved in a 40 ml solution of 100% nitric acid under an inert nitrogen atmosphere and at a temperature of about zero (0) degrees Celsius;

wherein there is added forty (40) milliliters of a 100 percent trifluoroacetic anhydride solution drop wise at such a rate as to keep the temperature of the solution below ten (10) degrees Celsius;

further wherein the solution is allowed to warm to from about 20 C to about 26 C with stirring for about two (2) hours until the precipitant is settled; and wherein the precipitant is washed with anhydrous dichloromethane, dried under vacuum at 10 torr with a yield of about 1.89 grams (5.86 mmol, 72%) of tetranitroglycoluril (TNGU).

9. A process according to claim 8 where the nitrimino moiety comprises N,N'-dinitrotetrahydroimidazo[4,5-d]imidazole-2,5(1H,3H)diimine.

10. A process according to claim 9 wherein the peak decomposition of the TNGU is from about 217 to about 220° C. as measured by a differential scanning calorimeter (DSC).

11. A process according to claim 8 where the nitrimino moiety comprises N-nitrotetrahydroimidazo[4,5-d]imidazole-2,5(1H,3H)diimine hydrochloride.

12. A process according to claim 11 wherein the peak decomposition of the TNGU is from about 217 to about 220° C. as measured by a differential scanning calorimeter (DSC).

13. A process according to claim 8 where the nitrimino moiety comprises and N-nitrotetrahydroimidazo[4,5-d]imidazole-2,5(1H,3H)diimine nitrate.

14. A process according to claim 13 wherein the peak decomposition of the TNGU is from about 217 to about 220° C. as measured by a differential scanning calorimeter (DSC).

* * * * *